United States Patent [19]

Galin

[11] Patent Number: 4,731,080

[45] Date of Patent: Mar. 15, 1988

[54] COATED INTRAOCULAR LENS

[76] Inventor: Miles A. Galin, 823 United Nations Plaza, New York, N.Y. 10017

[21] Appl. No.: 865,381

[22] Filed: May 20, 1986

Related U.S. Application Data

[63] Continuation-in-part of Ser. No. 692,672, Jan. 18, 1985, abandoned.

[51] Int. Cl.$^4$ ............................................. A61F 2/16
[52] U.S. Cl. ......................................... 623/6; 623/66; 427/2
[58] Field of Search ...................... 623/6, 66; 502/158; 427/2, 54.1, 93; 522/100; 525/531; 351/160 R, 160 H

[56] References Cited

U.S. PATENT DOCUMENTS

| | | | |
|---|---|---|---|
| 3,279,996 | 10/1966 | Long, Jr. et al. | 623/2 X |
| 3,566,874 | 3/1971 | Shepherd et al. | 351/160 H |
| 4,240,163 | 12/1980 | Galin | 623/6 |
| 4,260,725 | 4/1981 | Keough et al. | 351/160 H X |
| 4,338,377 | 7/1982 | Beck et al. | 428/429 X |
| 4,647,282 | 3/1987 | Fedorov et al. | 351/160 R X |

FOREIGN PATENT DOCUMENTS 2556665  6/1977  Fed. Rep. of Germany .......... 623/6

Primary Examiner—Richard J. Apley
Assistant Examiner—Alan W. Cannon
Attorney, Agent, or Firm—Brumbaugh, Graves, Donohue & Raymond

[57] ABSTRACT

An improved intraocular lens is coated with a non-smudging biologically compatible hydrophobic cross-linked vinyl-containing silicone polymer coating material, such as polymethylvinyl siloxane or polymethylphenylvinyl siloxane. The coating material is inert, does not smudge upon contact with another surface, reduces damage on contact with the intraocular tissue, particularly the endothelium, and prevents intraocular lens induction of inflammation. The coating material or matrix preferably contains at least one optically compatible medicament which can be gradually and controllably released therefrom with time and which makes the lens suitable for implantation in both the phakic and aphakic eye. The coating material may further contain a small amount of fine particle size fumed silica.

22 Claims, No Drawings

COATED INTRAOCULAR LENS

SPECIFICATION

This application is a continuation-in-part application of U.S. application Ser. No. 692,672, filed Jan. 18, 1985 (now abandoned).

BACKGROUND OF THE INVENTION

The present invention relates to an ophthalmic prosthetic device and more particularly to an anti-reactive coated intraocular lens.

As is well known in the field of ophthalmology, an intraocular lens, when surgically implanted, is designed to replace a previously or simultaneously removed cataractous lens. In addition, it is contemplated that such lenses can be placed in the phakic eye to compensate for refractive errors. The optical portion of such lenses may be of glass; a silicone polymer; an acrylic polymer, such as polymethyl methacrylate or polyhydroxyethyl methacrylate; or any combination thereof. The optical portion of the intraocular lens may also be made of copolymers of methyl methacrylate and ethyl acrylate or acrylic type monomers; copolymers of siloxanylalkyl acrylates and methacrylates; copolymers of fluoroacrylates and methacrylates; polysulfones; and polymers and copolymers of 2-hydroxyethyl methacrylate, glyceryl methacrylate, 2-hydroxypropyl methacrylate, methacrylic acid, acrylic acid, 2-acrylamido-2-methylpropane sulfonic acid, styrene sulfonic acid, acrylamide, methacrylamide, N-vinylpyrrolidone, diacetone acrylamide, 2-vinylpyridine, 4-vinylpyridine, 2-methyl-5-vinylpyridine, N-(2-methacryloyloxyethyl)-N,N-dimethylamine and N-(3-acrylamidopropyl)-N,N-dimethylamine. It is also possible for the intraocular lens to contain an ultraviolet absorber. These are presumably biologically neutral materials. The optical portion may have supports of the same nature, or may be supported by loops made of nylon, polypropylene, metal, polymethyl methacrylate or methyl methacrylate copolymers with other acrylic monomers.

An intraocular lens is small, with most anterior and posterior chamber lenses having an overall diameter of approximately 12-14 mm, if in a single piece of glass, silicone or plastic, with an optical diameter of 4 mm to 6 mm. Tip-to-tip diameters of looped anterior and posterior chamber lenses are approximately 12 mm to 15 mm. Iris support lenses usually have 8-10 mm loop diameters. The center thickness and posterior radii of the optical portion vary according to the power desired and the material utilized. An intraocular lens may weigh up to 25 mg in air, or 0.5 mg to 4 mg in aqueous medium. The intraocular lenses are commercially available from a variety of companies throughout the world.

Although the implantation of intraocular lenses has constituted an appreciable surgical advance, their use can still be improved upon significantly. For example, implantation of an intraocular lens may cause immediate or late damage to the corneal endothelium, immediate or late inflammatory responses to the anterior segment of the eye, immediate or late inflammatory responses to the posterior segment of the eye, and immediate or late secondary fibrosis and/or neovascularization. All in all, flare, white cells, vitreous reaction, cystoid macular edema, hypopyon, uveitis and secondary glaucoma are occurrences that may be present immediately or in a delayed manner after implantation and have become an ever-increasing problem.

When an intraocular lens is inserted into the eye, the mechanics of insertion may lead to temporary adhesion of the lens to delicate intraocular structures and damage to these structures ensues either immediately or is manifested in the long term. When in position, lenses may cause adhesions and fibrosis of a progressing nature, damaging intraocular tissues and making removal of such a lens a complex, dangerous surgical procedure. In particular, if such lenses are used in phakic eyes, damage to the clear lens may result negating the benefits of the operation. Coating such a lens with a coating material which would fill in the microscopic crevices that are present, no matter how well the lens is polished, softens the surface, changes its surface tension, and changes the contact angle. Such a coating will alter the abrasive potential of a lens and reduce the trauma of insertion and maintenance. Secondly, if this coating is physiologically inert and acts as a barrier, it can reduce the inflammatory potential of intraocular lenses and the dangerous sequelae resulting therefrom. Further, the coated lens may act as a therapeutic agent and may be used to elute materials that act as therapeutic agents to prevent and treat secondary reactions mentioned above.

U.S. Pat. No. 4,170,043 discloses coated intraocular lenses made of an acrylic resin wherein the coating is to prevent adhesion of the intraocular lens to the corneal endothelium, the coating being polyvinylpyrrolidone, polyvinyl alcohol, hydroxypropyl cellulose, hydroxypropyl methylcellulose, dextran, hydroxyethyl starch, methylcellulose or Jaguar (guar gum). However, some of these coatings caused inflammatory reactions and proved to be unsatisfactory in clinical practice.

Published West German patent application No. 2,556,665 discloses coated intraocular lenses wherein the coating is a silicone rubber, such as methyl or methylphenyl siloxane. However, such siloxane polymers cannot be crosslinked using ultraviolet light irradiation plus either a photosensitizer or a peroxide and hence the uncrosslinked siloxane coatings smudge upon contact with another surface.

U.S. Pat. No. 4,240,163 discloses coated intraocular lens wherein the coating is a compatible medicament. However, such coating materials cannot be gradually and controllably released from the intraocular lens surface with time, but rather they are generally rapidly released therefrom in the presence of the aqueous humor occupying the anterior and posterior chambers of the eye.

SUMMARY OF THE INVENTION

Accordingly, it is the principal object of the present invention to provide an improved intraocular lens which will overcome the above-mentioned problems in the use of an intraocular lens.

In accordance with the present invention, there is provided an improved intraocular lens coated with a non-smudging biologically compatible hydrophobic crosslinked vinyl-containing silicone polymer coating material. In a preferred embodiment of the present invention, the coating material contains at least one optically compatible medicament which can be gradually and controllably released therefrom with time and which makes the lens suitable for implantation in both the phakic and aphakic eye.

DETAILED DESCRIPTION OF THE INVENTION

As noted above, the improved intraocular lens of the present invention is coated with a non-smudging biologically compatible hydrophobic crosslinked vinyl-containing silicone polymer coating material. Preferably the coating material contains at least one optically compatible medicament which can be gradually and controllably released therefrom with time and which makes the lens suitable for implantation in both the phakic and aphakic eye.

The coating constitutes from about 0.001% to about 20% by weight of the intraocular lens. The coating has a thickness of from about 10 Å to about $10^6$ Å. In the preferred embodiment of the present invention, the medicament constitutes from about 0.001% to about 20% by weight of the coating material.

The non-smudging biologically compatible hydrophobic crosslinked vinyl-containing silicone polymer used in the present invention can be, for example, polymethylvinyl siloxane or polymethylphenylvinyl siloxane. This latter material is a Dow Corning product sold as Silastic MDX-4-4210. On the other hand, siloxane polymers not containing a vinyl group, such as polydimethyl siloxane and polymethylphenyl siloxane, cannot be used as the coating material in the present invention, because, as noted above, such siloxane polymers cannot be crosslinked using ultraviolet light irradiation plus either a photosensitizer or a peroxide and hence the uncrosslinked siloxane coatings smudge upon contact with another surface.

One or more suitable medicaments are preferably present in the biologically compatible coating material or matrix, provided the medicaments are optically compatible with the intraocular lens coating material so as to form optically clear coatings. Suitable anticoagulant or antiinflammatory medicaments can be incorporated with sulfated polysaccharides, such as a hyaluronate, xylan sulfate, chitosan sulfate, chondroitin sulfate and dextran sulfate. Heparin and, preferably, low molecular weight heparin, as well as other antiinflammatory agents, such as steroids, can be utilized. In addition, since low molecular weight heparin reduces platelet agglutination and is known to inhibit complement activity, white cell agglutination would be reduced and the enzymatic lysosomal released ingredients of white cells would have less opportunity to degrade the delicate intraocular content. Consequently, but not limited to, low molecular weight heparin can be used to reduce white cell responses inside the eye. Other agents, of course, that do the same can be used.

The coatings and a compatible medicament can be blockers of the standard complement system and the indirect complement system, which activate a whole chain of inflammatory sequences including certain white cell reactions. Certain blockers are often used topically or systemically to prevent the complications listed above. Such anticomplement agents as ethacrylic acid and prostaglandin inhibitors, and certain steroids, such as dexamethasone, can be used in this regard. However, these agents are used to suppress induced inflammation, while the coatings per se do not or only minimally induce the inflammatory sequences as compared to noncoated lenses. In addition, antibacterial agents, such as gentamicin, can also be utilized in the coatings to be released in a predictable, predetermined fashion.

Commercially available heparin, which usually has a molecular weight of from about 12,000 to about 15,000 daltons, may lead to platelet agglutination. Consequently, low molecular weight heparin (a derivative or fraction) would be more suitable in the range of molecular weight of from about 2,500 to about 5,300 daltons and even somewhat higher. These low molecular weight heparins can be prepared by enzymatic hydrolysis or depolymerization of heparin with heparinase as disclosed in U.S. Pat. No. 3,766,167, or by depolymerizing either heparin residues or commercial porcine or bovine heparin by reacting the heparin material with a blend of ascorbic acid and hydrogen peroxide; the reaction products then being isolated and fractionated by precipitation using an organic solvent, such as ethanol, methanol, acetone, methyl ethyl ketone or dioxane.

The coating material on the intraocular lens may further contain a small amount of fine particle size fumed silica, such as Cab-O-Sil, to improve coating efficiency. Thus, the coating material may contain an amount up to about 20% by weight of the coating material of fumed silica particles having an average particle size of about 12 nanometers.

The coated intraocular lens can be prepared by traditional coating methods which yield an optically clear surface when the lens and its coatings are dried. Thus, the coating can be applied to the intraocular lens surface by either immersion (dip) coating, spray coating, layering, or spin coating. Preferably, a coating solution is spin cast upon a rotating intraocular lens. The coating can be applied to the top or bottom optical surfaces, either at the same time or in different intervals. It is possible to coat the loops at this time or in subsequent dipping, spraying or spin casting applications.

In using the silicone polymer coating material, it is not necessary to dissolve the silicone polymer in a solvent prior to coating, since such polymers can flow readily, although this dissolution can be done using an aliphatic hydrocarbon solvent when acrylic polymer-based intraocular lenses are coated. One or more medicaments are preferably added to the silicone polymer coating material prior to placement on the intraocular lens. This can be done directly into the silicone fluid or elastomer, or into the solution. Should the medicaments not dissolve in the silicone polymer or in the solution, a finely divided medicament in low concentration can be dispersed uniformly throughout the silicone polymer such that after coating the lens remains visually clear.

In using the silicone polymer coating, the silicone polymer at room temperature or at about 40° C.–60° C., preferably with at least one admixed medicament, is placed upon the intraocular lens surface. The silicone polymer cannot be left in its native form (uncrosslinked), but rather it must be crosslinked, for example, by using ultraviolet light irradiation plus a small amount of either a photosensitizer or a peroxide for an irradiation period of from 10 minutes to 3 hours. The ultraviolet light source can be either an Ultra Violet Products, Inc., B-100 lamp or a Hanovia Chemical and Manufacturing Co. variable intensity lamp type 8800, set for maximum intensity. The photosensitizer can be, for example, an azo initiator, such as azobisisobutyronitrile, while the peroxide can be, for example, benzoyl peroxide or dicumyl peroxide. Since the silicone polymer surface is hydrophobic, humid conditions will not normally adversely effect the lens, although such conditions could be detrimental to the medicament preferably present causing premature release of the medicament.

It has been found that the anticoagulant, antiwhite blood cells, anticomplement, antiinflammatory intraocular lens coatings of the present invention with or without medication can reduce damage to the corneal endothelium upon contact at the time of implantation and reduce the undesirable secondary effects of inflammatory cellular response. Both these preventatives reduce the potential for adhesions, synechias, inflammation, cystoid macular edema, vitritis, cyclitis, uveitis and all secondary effects of inflammation, including lens opacification in the phakic eye. Certain anticoagulant, antiinflammatory coatings with or without medication were found to inhibit blood clotting from occurring as well as white blood cell agglutination (hypopyon) in the anterior chamber and reduce inflammation in general. The prevention of white blood cell clumps on the lens may improve the patient's vision, reduce the need for other medication, and allow more rapid recuperation.

It is important to note that in accordance with the preferred embodiment of the present invention, wherein the coating material contains a medicament, the medicament can diffuse gradually from the coating material or matrix on the intraocular lens with time, the rate of release depending upon its molecular weight and the porous nature of the coating material or matrix. It is also possible to employ layers of coatings, wherein each layer can contain a different medicament. In this fashion, it is now possible to provide a timed-release of the desired therapeutic agent(s) or medicament(s). In the silicone polymer coatings, the medicament will be released in a controlled fashion until its supply is exhausted. These features or advantages of the medicament-containing coated intraocular lens of the present invention are not characteristic of the medicament coated intraocular lens of the above-mentioned U.S. Pat. No. 4,240,163.

In regard to the silicone polymer coating, a silicone polymer coating on a traditionally hard intraocular lens, such as that made from polymethyl methacrylate or methyl methacrylate copolymers with other monomers, gives the desirable benefits of a soft, silicone-based intraocular lens but in addition has the greater handling and optical properties of a hard lens.

What is claimed is:

1. An intraocular lens coated with a non-smudging biologically compatible hydrophobic crosslinked vinyl-containing silicone polymer coating material selected from the group consisting of polymethylvinyl siloxane and polymethylphenylvinyl siloxane.

2. An intraocular lens defined by claim 1 wherein the coating material contains at least one optically compatible medicament which can be gradually and controllably released therefrom with time and which makes the lens suitable for implantation in both the phakic and aphakic eye.

3. An intraocular lens defined by claims 1 or 2 wherein the coating constitutes from about 0.001% to about 20% by weight of the intraocular lens.

4. An intraocular lens defined by claims 1 or 2 wherein the coating has a thickness of from about 10 Å to about $10^6$ Å.

5. An intraocular lens defined by claim 2 wherein the medicament constitutes from about 0.001% to about 20% by weight of the coating material.

6. An intraocular lens defined by claim 1 wherein the hydrophobic crosslinked vinyl-containing silicone polymer coating material is polymethylvinyl siloxane.

7. An intraocular lens defined by claim 1 wherein the hydrophobic crosslinked vinyl-containing silicone polymer coating material is polymethylphenylvinyl siloxane.

8. An intraocular lens defined by claim 2 wherein the medicament is an anticoagulant.

9. An intraocular lens defined by claim 2 wherein the medicament is an antiinflammatory agent.

10. An intraocular lens defined by claim 2 wherein the medicament is an anticomplement agent.

11. An intraocular lens defined by claim 2 wherein the medicament is an antibacterial agent.

12. An intraocular lens defined by claim 2 wherein the medicament is ethacrylic acid.

13. An intraocular lens defined by claim 2 wherein the coating material also contains a sulfated polysaccharide.

14. An intraocular lens defined by claim 13 wherein the sulfated polysaccharide is heparin having a molecular weight of from about 12,000 to about 15,000 daltons.

15. An intraocular lens defined by claim 13 wherein the sulfated polysaccharide is low molecular weight heparin having a molecular weight of from about 2,500 to about 5,300 daltons.

16. An intraocular lens defined by claim 13 wherein the sulfated polysaccharide is dextran sulfate.

17. An intraocular lens defined by claim 13 wherein the sulfated polysaccharide is chondroitin sulfate.

18. An intraocular lens defined by claim 13 wherein the sulfated polysaccharide is chitosan sulfate.

19. An intraocular lens defined by claim 13 wherein the sulfated polysaccharide is xylan sulfate.

20. An intraocular lens defined by claim 13 wherein the sulfated polysaccharide is a hyaluronate.

21. An intraocular lens defined by claims 1 or 2 wherein the coating material contains a small amount of fine particle size fumed silica.

22. An intraocular lens defined by claim 21 wherein the coating material contains an amount up to about 20% by weight of the coating material of fumed silica particles having an average particle size of about 12 nanometers.

* * * * *